US008676300B2

(12) United States Patent
Strommer et al.

(10) Patent No.: US 8,676,300 B2
(45) Date of Patent: Mar. 18, 2014

(54) METHOD AND SYSTEM FOR NAVIGATING THROUGH AN OCCLUDED TUBULAR ORGAN

(75) Inventors: Gera Strommer, Haifa (IL); Uzi Eichler, Haifa (IL); Adrian Herscovici, Haifa (IL)

(73) Assignee: MediGuide Ltd., Haifa (IL)

( * ) Notice: Subject to any disclaimer, the term of this patent is extended or adjusted under 35 U.S.C. 154(b) by 1162 days.

(21) Appl. No.: 11/856,415

(22) Filed: Sep. 17, 2007

(65) Prior Publication Data

US 2008/0091171 A1 Apr. 17, 2008

Related U.S. Application Data

(60) Provisional application No. 60/845,347, filed on Sep. 18, 2006.

(51) Int. Cl.
*A61B 6/00* (2006.01)

(52) U.S. Cl.
USPC ........... 600/431; 600/407; 600/415; 600/429; 600/434; 600/439

(58) Field of Classification Search
None
See application file for complete search history.

(56) References Cited

U.S. PATENT DOCUMENTS 6,690,816 B2 * 2/2004 Aylward et al. ............... 382/128
(Continued)

FOREIGN PATENT DOCUMENTS

| JP | 2004-283373 A | 10/2004 |
| WO | 2005/084122 A2 | 9/2005 |
| WO | 2006/027781 A2 | 3/2006 |

OTHER PUBLICATIONS

Castro, Marcelo A. et al., "Patient-Specific Computational Modeling of Cerebral Aneurysms with Multiple Avenues of Flow from 3D Rotational Angiography Images", *Academic Radiology*, vol. 12, Issue 7 Jul. 2008, Abstract only.

(Continued)

*Primary Examiner* — Long V. Le
*Assistant Examiner* — Nicholas Evoy
(74) *Attorney, Agent, or Firm* — Dykema Gossett PLLC

(57) ABSTRACT

A method generates a three dimensional (3D) model of a tubular organ having an occluded segment. The occluded segment adjoins a proximal segment at a proximal end thereof, and a distal segment at a distal end thereof. The procedures included injecting a first dye injection into the tubular organ, the first dye approaching a first end of the occluded segment. Multiple first-injection two-dimensional (2D) images of the tubular organ are acquired, each acquired from a different perspective, the first-injection 2D images further acquired with a respective organ timing signal reading. A second dye is injected into the tubular organ, the second dye approaching a second end of the occluded segment. Multiple second-injection 2D images are acquired of the tubular organ, each acquired from a different perspective, the second-injection 2D images further acquired with a respective organ timing signal reading. Superimposed 2D images are generated, one for each of the perspectives, each of the superimposed 2D images including the proximal segment and the distal segment. The boundary regions of the proximal segment and the distal segment in the superimposed 2D images are determined. The boundary regions of the occluded segment in the superimposed 2D images are determined by interpolating between the boundary regions of the proximal segment and the distal segment. A 3D model of the tubular organ from the superimposed 2D images is generated and a 3D center line of the tubular organ is determined, the 3D center line passing through the proximal segment, through the occluded segment and through the distal segment.

19 Claims, 8 Drawing Sheets

(56) References Cited

U.S. PATENT DOCUMENTS

2005/0107688 A1* 5/2005 Strommer .................. 600/424
2005/0197557 A1 9/2005 Strommer et al.
2006/0064006 A1 3/2006 Strommer et al.

OTHER PUBLICATIONS

Castro et al., "Patient-Specific Computational Modeling of Cerebral Aneurysms with Multiple Avenues of Flow from 3D Rotational Angiography Images," Academic Radiology, Reston, VA, US, vol. 13, No. 7, Jul. 2006, pp. 811-821.

* cited by examiner

METHOD AND SYSTEM FOR NAVIGATING THROUGH AN OCCLUDED TUBULAR ORGAN

FIELD OF THE DISCLOSED TECHNIQUE

The disclosed technique relates to vascular treatment devices, in general, and to methods and systems for navigating through an occluded blood vessel, in particular.

BACKGROUND OF THE DISCLOSED TECHNIQUE

The accumulation of plaque deposits within a blood vessel gradually leads to a blockage or occlusion of the vessel. The resulting abnormal narrowing of the vessel, known as stenosis, can cause several complications. In particular, stenosis of the coronary arteries restricts blood flow to and from the heart (i.e., ischemia), potentially resulting in serious damage to the heart tissue. The progressive thickening and hardening of the arterial wall due to plaque formation in the arterial lumen is known as atherosclerosis. Atherosclerosis is responsible for many coronary artery diseases and syndromes, such as angina pectoris, cardiac arrest and myocardial infarction (i.e., heart attacks), as well as strokes and leg gangrene.

Treatment of occluded blood vessels generally involves minimally invasive angioplasty procedures, which aims to physically expand the constricted artery. Prior to the treatment, a guidewire must be advanced beyond the occluded area to permit passage of a catheter along the guidewire. Once the guidewire is positioned beyond the blockage, the catheter, together with a balloon or stent, is passed over the guidewire and angioplasty is carried out. Generally, a fluoroscopic procedure (e.g., angiography) is initially performed, to provide a visual representation of the occluded vessel for use by the physician to navigate the guidewire. As blood vessels are normally apparent in X-ray images, such fluoroscopic image of the vessel is available due to dye injection into the inspected vessel, enabling the visualization of the course of the dye flow through the vessel lumen. If the blood vessel is only partially occluded, and there is a sufficient gap within the occluded area to allow passage of a guidwire, then it is possible to advance the guidewire to the target area, and perform medical procedures, while using the guidewire for direction and support. In the case of total occlusion, however, the guidewire is prevented from advancing through and beyond the occluded region of the artery. The total occlusion prevents the physician from identifying the exact course of the occluded artery on the fluoroscopic images, due to the fact that there is no dye flows through the occluded portion of the vessel, therefore this portion of the vessel is not visible on the fluoroscopy. Thus, it is very difficult to cross the entire length of the occlusion, and to determine the optimal manipulations required to correctly navigate the guidewire within the artery. Improper manipulation of the guidewire may cause a localized dissection of the intimal or subintimal layer of the arterial wall, and even complete perforation of the arterial wall, resulting in severe complications and failure of the procedure. Thus, minimally invasive medical procedures in cases of total occlusion of the artery have a significantly lower success rate and a higher complication rate, as compared to partial occlusion or artery narrowing.

Existing techniques to deal with advancing a guidewire through an occluded blood vessel include, for example, cutting atherectomy catheters, which attempt to penetrate through the occlusion. Another known technique includes pushing a guidewire into the occluded blood vessel, and trying to brake through the whole length of the total occlusion, based on an imaginary course of the occlusion. The guidewires used for penetrating total occlusions usually exhibit stiffness, and may perforate the vessel wall when force is applied thereto, thereby generating a false lumen. Thus, physicians may be hesitant to use such force in pushing the guidewire through the occlusion, as they do not surely follow the actual course of the occluded vessel. If the guidewire cannot be advanced beyond the occlusion, major invasive surgery may alternately be performed, such as bypass surgery. It is generally preferable to avoid such invasive therapeutic procedures, as they involve severe complications and trauma to the patient. Other known techniques for treatment of an occlusion, involve laser ablation, application of radiation pulses, or administering fluid to remove the occlusion. In some cases, a small cavity may remain open through the occluded vessel, through which a guidewire may be inserted. However, it is usually very difficult for a physician to keep a CTO wire (a stiff wire) in the center of the vessel, due to the fact that the occluded portion of the vessel is actually not apparent in the fluoroscopic images.

U.S. Pat. No. 5,423,846 to Fischell entitled "Dottering auger catheter system", is directed to a catheter system for penetrating a vessel blockage (i.e., total occlusion) in the human body, to create an initial passageway prior to a vessel opening procedure, such as balloon angioplasty or atherectomy. The catheter system includes a centering catheter, and a dottering auger catheter (DAC). The DAC includes a steel tube on the proximal end, a flexible catheter section, and a self-tapping auger screw on the distal end. The screw has a conical section that tapers off to a sharp point. The proximal end of the steel tube extends outside the body of the patient. A handle is attached to the proximal end of the steel tube. The centering catheter includes a balloon at its distal end. The centering catheter has a central lumen, through which the DAC is inserted, and a second lumen, through which a fluid can be passed, to inflate the balloon.

After angiography is performed to indicate a blockage in an artery of the patient, a guide wire is advanced toward the artery until the distal end of the guide wire is adjacent to the proximal surface of the blockage. The centering catheter is then advanced over the guide wire, until the distal end of the centering catheter contacts the proximal surface of the blockage. The guide wire is removed, and the balloon of the centering catheter is inflated, thereby centering the distal end of the centering catheter within the artery (and reducing the possibility that the screw will penetrate through the wall of the artery). A contrast medium is injected through the central lumen of the centering catheter to verify the position of the centering catheter of the artery, and the length of the blockage. The DAC is advanced through the centering catheter, until the distal end of the DAC contacts the proximal surface of the blockage. The auger screw is advanced beyond the length of the blockage, by simultaneously applying a rotational torque and a push force to the DAC via the handle. The auger screw is removed, and a contrast medium is injected through the central lumen of the centering catheter to verify that the DAC created a pathway through the blockage. Another guide wire is advanced through the centering catheter and the created pathway. The centering catheter is removed, and a balloon angioplasty or atherectomy procedure is performed.

U.S. Pat. No. 6,210,408 to Chandrasekaran et al entitled "Guide wire system for RF recanalization or vascular blockages", is directed to a method and system for recanalizing an occluded blood vessels within the vasculature of a patient. The system includes a centering catheter, a guide wire, and a radio frequency (RF) generator. The guide wire includes an ablation tip on the distal end. The centering catheter includes an elongate catheter body having a guide wire lumen, and a centering mechanism (e.g., an elongated, inflatable balloon). The guide wire is coupled with the RF generator. The RF generator is further coupled with a patient return electrode, and with a footswitch.

The return electrode (e.g., a pad with a substantially large area) is attached to the patient, to maximize the delivery of the RF energy to the target tissue. The guide wire is inserted and routed through the patient vasculature, until the ablation tip is disposed proximal to the total occlusion. The centering catheter is advanced over the guide wire, until the centering mechanism (i.e., balloon) is disposed adjacent to the total occlusion. A contrast agent is conveyed into the deflated balloon, to enable easier fluoroscope detection of the balloon. An inflation medium is conveyed into the balloon, inflating the balloon until it is in secure contact with the blood vessel. The balloon maintains the guide wire along the centerline of the blood vessel, such that the ablation tip is substantially centered as it contacts the occlusion. The RF generator is then activated by depressing the footswitch, delivering RF energy to the ablation tip. A sufficiently high voltage potential is produced to initiate a spark erosion process, thereby ionizing the liquid contained in the occlusive material. The ionization converts the occlusive material into a plasma state, and the resultant particulate matter is safely absorbed by the blood stream. After the spark erosion process is initiated, a lower voltage potential is applied to maintain plasma conversion. The output power of the RF energy is a function of the relative impedance between the ablation tip and the load impedance. The voltage, impedance and electrode geometry is selected such that the spark erosion process is initiated when a load impedance that indicates occlusive material is reached (i.e., above the impedance of blood or healthy vessel tissue). The ablation tip includes at least one discontinuous feature (e.g., an edge or point), to facilitate sparking between the ablation tip and the tissue. As the RF energy is applied, the guide wire is distally advanced through the center of the occlusion. The centering catheter is removed, and a therapeutic device for treatment of the occlusion (e.g., a PCTA catheter) is introduced over the guide wire.

U.S. Pat. No. 6,643,533 to Knoplioch et al entitled "Method and apparatus for displaying images of tubular structures", is directed to a method and apparatus for the display and analysis of vascular images acquired through a medical imaging system. The method may be used for displaying a stenosis of a vessel in the patient body, determining the smallest cross-section of the vessel. The method includes the step of first identifying a centerline of the vessel. The next step involves selecting a local center point on the centerline. The following step involves obtaining a cross-section plane normal to the local center point, and identifying a contour of the vessel within the cross-sectional plane. The next step involves sequentially measuring the lengths of various segments across the contour, where each segment intersects the local center point. The shortest segment is identified out of all the taken measurements. The next step involves determining an imaging plane showing the stenosis. The imaging plane is defined by the shortest segment and a local axis tangent to the centerline at the local center point. Subsequently, the imaging plane is displayed, showing a cross-section of the vessel which indicates the stenosis. An image acquisition may then be performed relative to the imaging plane. For example, an X-ray acquisition may be performed, with the perpendicular to the imaging plane as a line of sight and the local center point as a target. A magnetic resonance (MR) system may be used to acquire image slices, with the location of the slice being the imaging plane or another plane that is translated from the imaging plane by a selected distance.

U.S. Pat. No. 6,824,550 to Noriega et al entitled "Guidewire for crossing occlusions or stenosis", is directed to a system and method for crossing stenosis, partial occlusions or total occlusions in a body lumen. The system includes a hollow guidewire, a drive shaft, a housing, and a drive motor. The drive shaft moveably extends within the axial passage of the guidewire. The drive motor is coupled with the drive shaft. The drive motor is further electrically coupled with a control system and a power supply. The proximal end of the guidewire is coupled with the housing, which is attached to an input device. The input device controls the rotation and axial movement of the drive shaft. The distal tip of the drive shaft has a shaped profile. The shape may be configured optimally for the type of occlusion to be penetrated. The distal tip may be shaped or deflected from the longitudinal axis of the guidewire, such that the rotation of the drive shaft creates a path radius that is larger than, the same, or smaller than the radius of the distal end of the guidewire.

A user advances the hollow guidewire along the body lumen, to the target site. The user activates the drive motor to rotate and advance the drive shaft, from an axially retracted position to an axially extended position, thereby creating a path through the occlusion. The user may also rotate the drive shaft manually for slow speed rotation. As the distal tip is rotated, the distal tip macerates the clot at the target site, separating the clot from the wall of the body lumen. The user may aspirate the macerated clot through the guidewire working channel, or deliver a thrombylatic fluid to dissolve the macerated clot. The guidewire may further include an access or support system, such as an infusion or aspiration catheter, to aspirate the target site or to infuse therapeutic or diagnostic materials therein. The hollow guidewire may also be used to advance an atherectomy device into or adjacent to the path of the occlusion. The distal portion of the drive shaft may be radiopaque, to allow a physician to track the position of the drive shaft via fluoroscopy.

U.S. Pat. No. 6,911,026 to Hall et al entitled "Magnetically Guided atherectomy", is directed to a magnetically guided catheter for treating a totally occluded arterial vasculature. An energy source is coupled to the distal tip of the catheter. The distal tip of the catheter includes a magnetically active element. The catheter is guided to the treatment site via a guide wire and sheath, which also includes a magnetic element. The catheter may be a thermal catheter, which is heated by an RF source, in a bipolar or monopolar configuration. Alternatively, the catheter is resistance heated or laser heated. The catheter may include a lumen, through which an imaging wire may be inserted, to visualize and locate the occlusion (e.g., using ultrasound imaging or fluorescence spectroscopy). A contrast agent may be injected between the sheath and catheter body, allowing the catheter to be viewed in the patient body. A cooling fluid may be injected to the catheter tip to regulate the temperature distribution.

The patient undergoes a preoperative scan (e.g., using MRI, CT, ultrasound imaging), and the preoperative data is loaded into a workstation console. During the treatment, an X-ray machine provides real-time biplane X-ray data of the patient, to the workstation. The catheter includes a fiducial marker, allowing the preoperative scan data and real-time scan data to be merged. The physician may select the location of the treatment site on the workstation, and the workstation computes the magnetic fields and gradients required to navigate the catheter to the selected location. An external magnet generates magnetic forces on the catheter tip, and the applied field and gradient orients the tip direction toward the selected location. The physician (or a robotic element) pushes on the proximal end of the catheter to advance the guidewire and sheath. The physical motion together with the magnetic orientation of the tip serves to position the catheter at the selected location.

BRIEF DESCRIPTION OF THE DRAWINGS

The disclosed technique will be understood and appreciated more fully from the following detailed description taken in conjunction with the drawings in which:

FIG. 4C is a schematic illustration of the 3D model of FIG. 4A, including a representation of an MPS sensor position and orientation, the orientation deviating from a 3D center line of the 3D model;

DETAILED DESCRIPTION OF THE EMBODIMENTS

Figure 2A:
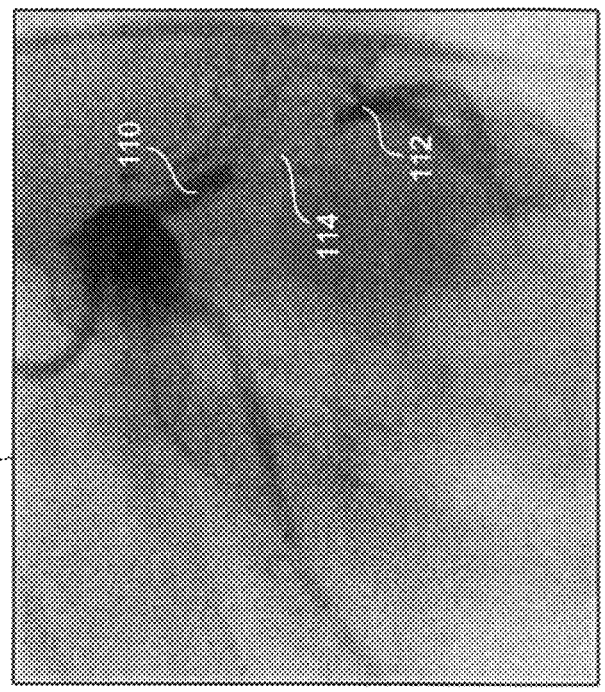
FIG. 2A is a detailed superimposed 2D image of an occlusion area, generally referenced 102, including a representation of a proximal segment and a distal segment of the occluded artery of the heart of FIG. 1.

The disclosed technique overcomes the disadvantages of the prior art by providing a method and system for navigating through an occluded tubular organ, by employing a three-dimensional (3D) model of the occluded tubular organ, a medical positioning system (MPS) registered with the 3D model, and an MPS enabled guidewire. A 3D model of an occluded blood vessel is generated, for example, by acquiring a plurality of two-dimensional (2D) images of the blood vessel from different perspectives and reconstructing the 3D model there from. The 2D images include representations of a proximal segment and a distal segment of the blood vessel, and do not include a representation of the occluded segment (since no blood flows there through). A representation of the overall occluded vessel can be obtained by superimposing two 2D fluoroscopic images, each including a representation of another segment of the blood vessel. The boundary regions of the proximal segment and the distal segment are identified in the superimposed 2D images, by employing image processing techniques. The boundary regions of the occluded segment can not be identified in the acquired images. Thus, the boundary regions of the proximal segment and the distal segment are interpolated to determine an estimate of the boundary region of the occluded segment. The generated 3D model then includes a representation of the proximal segment, the occluded segment and the distal segment of the blood vessel. A 3D center line of the blood vessel is determined in the 3D model, passing through the proximal segment, the occluded segment and the distal segment.

A guidewire is inserted into the blood vessel, having a Medical Positioning System (MPS) sensor mounted on the distal tip thereof. The position and orientation of the distal tip of the guidewire are determined by an MPS at a plurality of positions along the blood vessel. The 3D model is registered with the MPS 3D coordinate system. The guidewire tip approaches one end of the occluded segment. The guidewire tip is navigated through the occluded segment along a safe trajectory defined by the 3D center line. If the guidewire tip deviates from the safe trajectory, a real time indication is produced, to notify the user advancing the guidewire, that the course of the guidewire may be unsafe and should be adjusted to align with the safe trajectory, or to refrain from further advancing the guidewire. Once the guidewire tip is positioned beyond the occluded segment, a catheter, including a balloon or a stent, can be passed over the guidewire and angioplasty may be carried out.

It is noted, that advancing of the guidewire may be performed by a robotic system, instead of a human operator, or a combination of the robotic system and the human user, as described in US patent application publication no. US2005-0197557A1, incorporated by reference herewith. It is further noted, that the 3D model may be obtained by employing other known methods, such as 3D CT, Magnetic Resonance Imaging (MRI), 3D Ultrasound, and the like. When such a 3D model is used, the 3D model is segmented and registered with the MPS coordinate system, in order to generate the 3D center line or trajectory.

The term "tubular organ", refers to a bodily organ, having an elongated tubular shape, such as a blood vessel, an artery, a heart cavity, (e.g., atrium or chamber), and the like. Accordingly, the terms tubular organ, blood vessel, artery, and the like, are interchangeable. The term "boundary region", refers to the area representing the blood vessel walls as they appear in the acquired 2D images. The term "user", refers to a person performing the described medical procedure, a physician, a robot, and the like. The term "catheter", refers to a medical catheter adapted to be inserted into a tubular organ, such as a Guided Measurement Catheter (GMC), a diagnostic catheter (e.g., Ultra Sound imaging catheter) or a therapeutic catheter (e.g., stenting catheter or an ablating catheter).

Figure 1:
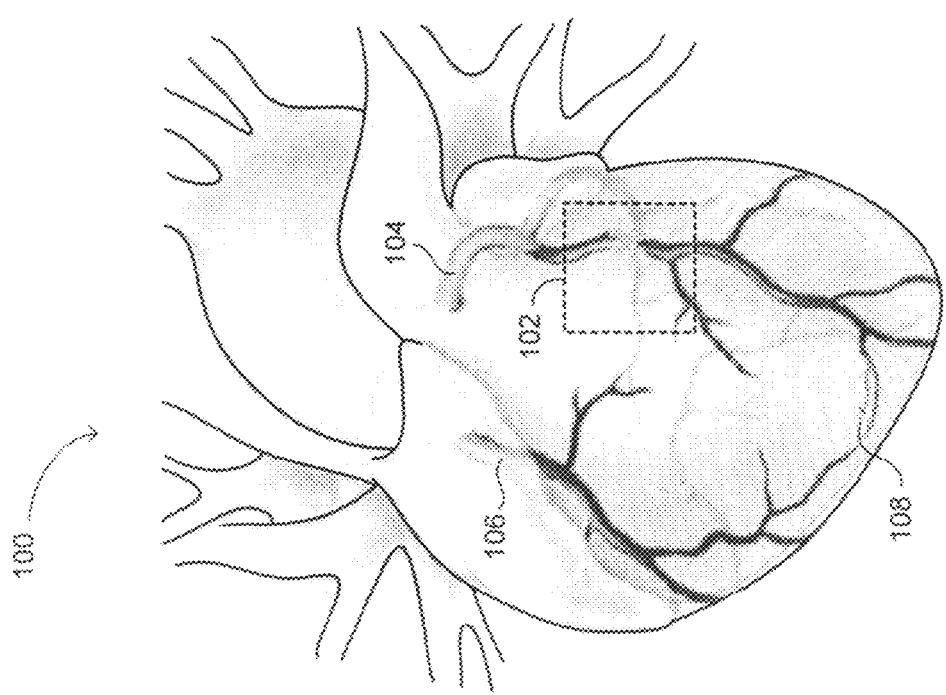
FIG. 1 is a schematic illustrative 3D model of a heart, generally referenced 100, having an occluded artery, to which the disclosed technique is applied.
Figure 2B:
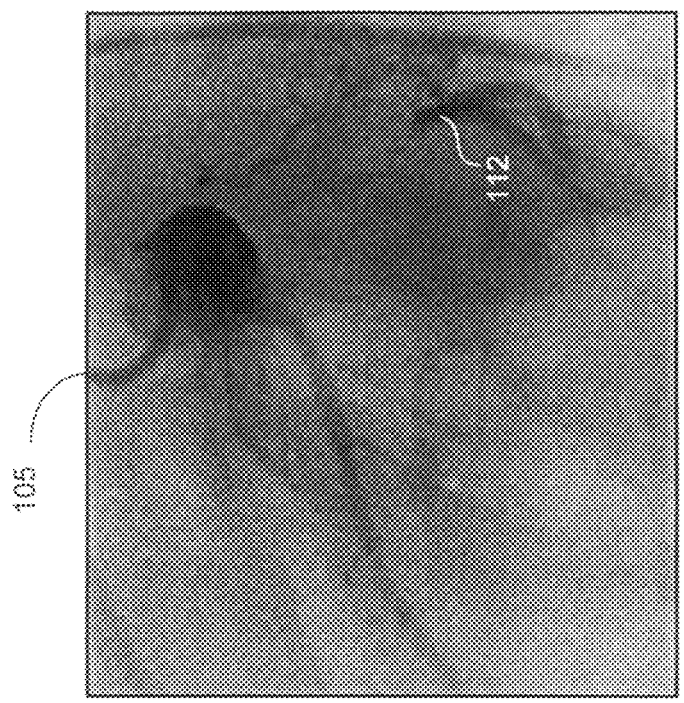
FIG. 2B is a first-injection 2D image of the occlusion area of FIG. 2A, including a representation of the proximal segment of the occluded artery of the heart of FIG. 1.
Figure 2C:
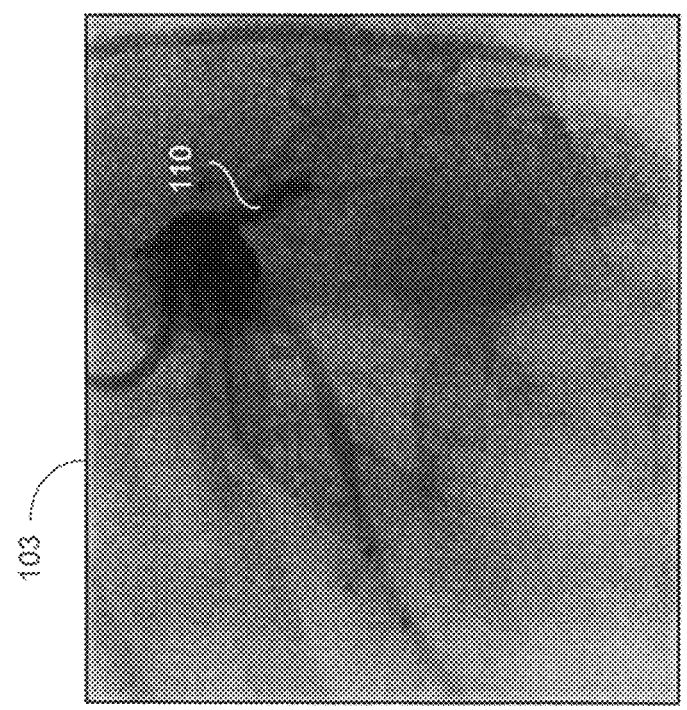
FIG. 2C is a second-injection 2D image of the occlusion area of FIG. 2A, including a representation of the distal segment of the occluded artery of the heart of FIG. 1.

Reference is now made to FIGS. 1, 2A, 2B and 2C. FIG. 1 is a schematic illustrative 3D model of a heart, generally referenced 100, having an occluded artery, to which the disclosed technique is applied. FIG. 2A is a detailed superimposed 2D image of an occlusion area, generally referenced 102, including a representation of a proximal segment and a distal segment of the occluded artery of the heart of FIG. 1. FIG. 2B is a first-injection 2D image of the occlusion area of FIG. 2A, including a representation of the proximal segment of the occluded artery of the heart of FIG. 1. FIG. 2C is a second-injection 2D image of the occlusion area of FIG. 2A, including a representation of the distal segment of the occluded artery of the heart of FIG. 1. The superimposed image of FIG. 2A can be generated by combining two 2D images (e.g., acquired by fluoroscopic angiography), each including a representation of another segment of the occluded artery of heart 100, such as the images of FIGS. 2B and 2C. Heart 100 includes an occluded artery 104, an unblocked artery 106 and a natural bypass 108. Heart 100 has an occlusion area 102, having an occluded segment of occluded artery 104 therein. With reference to FIG. 2A, occlusion area 102 has a section of artery 104 therein, including an occluded segment 114, adjoining a proximal segment 110 on the proximal end thereof, and a distal segment 112 on the distal end thereof. Occluded segment 114 is blocked in such a manner, that blood can not flow there through (i.e., 90%-100% occluded). Such a medical condition is also referred to as Chronic Total Occlusion (CTO), and it usually occurs due to the accumulation of plaque deposits from the blood flowing in the blood vessel. A physician treating heart 100 is aware of the existence of occluded segment 114, albeit this segment is not visible in the superimposed image of occlusion area 102, obtained by fluoroscopic angiography. Natural bypass 108 is consisted of small blood vessels (co-lateral vessels), allowing blood to flow from unblocked artery 106 to distal segment 112 of occluded artery 104. The blood vessels of natural bypass 108 are generated by angiogenesis (i.e., the formation of new blood vessels out of existing blood vessels). The blood vessels of natural bypass 108 may couple occluded artery 104, for example, with the distal part of the Left Anterior Descending (LAD) artery of the heart, or with the Right Coronary Artery (RCA).

A plurality of 2D images of occlusion area 102 is acquired, each image acquired from a different perspective. In an exemplary medical procedure, an angiogram of heart 100 is obtained, when a first fluoroscopic dye injection is administered into occluded artery 104, approaching occluded segment 114 through proximal segment 110. With reference to FIG. 2B, subsequent to the first injection, a first-injection 2D image 103 of occlusion area 102 is acquired from a first perspective, showing the blood vessels in heart 100, in which the fluoroscopic dye is present. First-injection 2D image 103 is obtained when an imaging radiation transmitter is placed on the one side of the body of the patient, and a radiation detector is placed on the opposite side of the body. The imaging radiation transmitter and imaging radiation detector can be integrated into a single imaging device, having the shape of the letter "C" (i.e., C-arm). A line drawn between the radiation transmitter and the radiation detector defines an optical axis of the imaging device. The term "perspective", as used herein, relates to the spatial orientation (i.e., vectorial direction) of the optical axis of the imaging device (i.e., the angle of the optical axis relative to the patient).

The areas, in which the fluoroscopic dye is present (i.e., where the blood flows), appear in the acquired image as darker than the areas in which no dye is present. Thus, proximal segment 110 is apparent in first-injection 2D image 103.

Since occluded segment 114 does not allow blood to flow there through, occluded segment 114 is not apparent in first-injection 2D image 103. Similarly, blood may not flow through distal segment 112, and it may not be apparent in first-injection 2D image 103. However, natural bypasses (not shown), such as natural bypass 108, may allow blood flowing in proximal segment 110 to reach distal segment 112. If such natural bypasses exist, then distal segment 112 shall be apparent in the first-injection 2D image. In order to allow the determination of a 3D model of the blood vessels of heart 100, at least another 2D image is acquired from another perspective, after the first injection. The difference between the first perspective and the other perspective (i.e., the angular difference between the vectorial direction of the optical axis in both perspectives) is at least 30°. Preferably, the difference between these perspectives is approximately 90°.

If distal segment 112 is not apparent in the first-injection 2D images, then a second contra-lateral fluoroscopic dye injection is administered into unblocked artery 106. Blood flowing through unblocked artery 106 may flow through natural bypass 108, and reach distal segment 112. With reference to FIG. 2C, subsequent to the second injection, a second-injection 2D image 105 of occlusion area 102 is acquired from a first perspective, showing the presence of the fluoroscopic dye in the blood vessels in heart 100. In this image, distal segment 112 is apparent, since blood containing the fluoroscopic dye flows there through, arriving from natural bypass 108. Proximal segment 110 is not apparent in second-injection 2D image 105, since no fluoroscopic dye flows there through after the second injection. Similarly to the first injection, another 2D image is acquired from a second perspective, after the second injection. It is noted, that the perspectives from which the 2D images are acquired subsequent to the first dye injection, are substantially the same as the perspectives from which 2D images are acquired subsequent to the second dye injection. It is noted, that the person performing the medical procedure described herein may have prior knowledge regarding the degree of blockage in occluded artery 104 (e.g., based on previous medical imaging, and the like). In this case, the person performing the medical procedure may administer the second dye injection and use the imaging device to acquire the second-injection 2D images, without analyzing the first-injection 2D images (i.e., acquisition of the second-injection 2D images unconditionally of the results of the first-injection 2D images).

The inspected tubular organ may move during the acquisition of the 2D images. More particularly, when the tubular organ is a coronary artery, such as occluded artery 104, the tubular organ is involved in a cyclic motion according to the cardiac cycle and respiration, caused by the pressurized flow of blood there through. Therefore, each of the dye-injection 2D images is acquired with a respective organ timing signal (i.e., ECG and respiration data), acquired simultaneously therewith (i.e., synchronizing). Thus, each acquired 2D image is associated with an organ timing signal reading, which is associated with a certain point in the cardiac cycle, respiratory cycle or both (i.e., time tagging). The organ timing signals can be detected by an Electrocardiogram (ECG) detector fitted with body surface electrodes. The respiration cycle can be detected, for example, by an MPS reference sensor, or sensor set, attached to the body of the patient.

Once both proximal segment 110 and distal segment 112 are apparent in the images acquired after the dye injections, the images are combined (e.g., first-injection 2D image 103 and second-injection 2D image 105), to create a superimposed image for each perspective used. Each of the superimposed images includes a representation of both ends of occluded segment 114. For example, if two images were acquired for each dye injection, from two different perspectives, then two superimposed images are obtained.

Figure 3A:
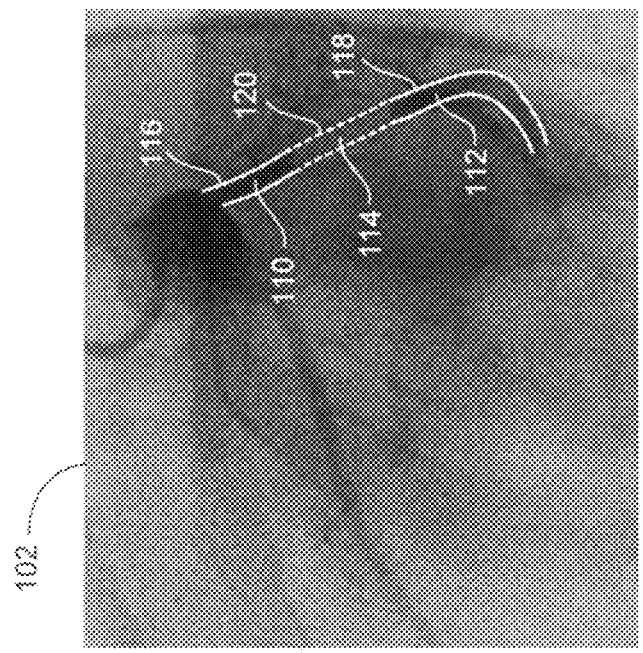
FIG. 3A is a superimposed 2D image of the occlusion area of FIG. 1, in which the boundary regions of the proximal segment and the distal segment are presented, according to another embodiment of the disclosed technique.
Figure 3B:
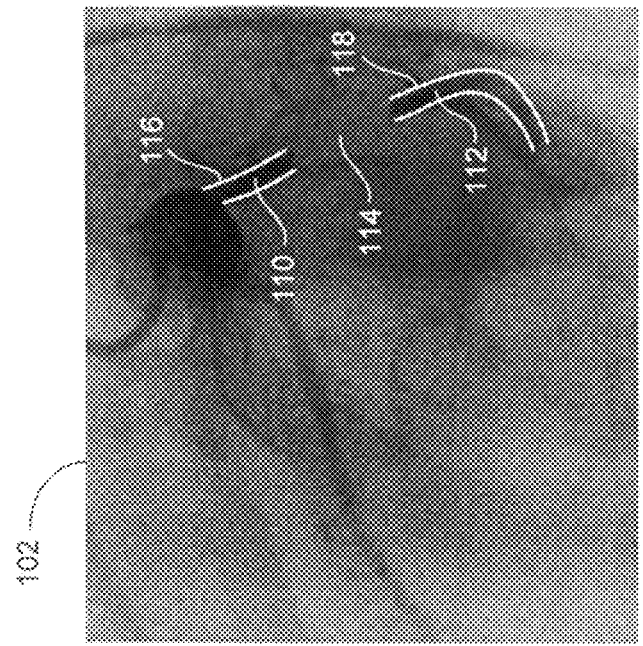
FIG. 3B is the image of FIG. 3A, in which the boundary regions of the occluded segment are additionally presented.

Reference is now made to FIGS. 3A and 3B. FIG. 3A is a superimposed 2D image of the occlusion area of FIG. 1, in which the boundary regions of the proximal segment and the distal segment are presented, according to another embodiment of the disclosed technique. FIG. 3B is the image of FIG. 3A, in which the boundary regions of the occluded segment are additionally presented. The following description relates to a single superimposed 2D image. However, the described method is performed on each of the superimposed 2D images, obtained from the acquired images subsequent to the fluoroscopic dye injections.

A boundary region 116 of proximal segment 110 and a boundary region 118 of distal segment 112, which appear in the superimposed image, are determined by using image processing techniques. For example, the image processing techniques can include edge detection or segmentation, in which certain segments or regions in the image, having properties distinct from their adjacent regions, are determined. The regions representing proximal segment 110 and distal segment 112 in the superimposed image are identified with respect to their surrounding regions, since they appear darker than the surrounding regions (i.e., where no fluoroscopic dye is present). The superimposed image of occlusion area 102 may be displayed to a user (e.g., a physician). The display includes a representation of boundary region 116 and boundary region 118 on the superimposed image. The user can then observe the determined boundary regions and adjust them, in case they do not seem to comply with the apparent boundary regions in the displayed image.

With reference to FIG. 3B, interpolation between boundary region 116 and boundary region 118, provides an estimate of a boundary region 120, depicted in dotted lines, of occluded segment 114. This interpolation can be performed by image processing of the superimposed image (e.g., by an image processor), or manually by the user (e.g., via a user input module). In the case where the superimposed image of occlusion area 102 is displayed to the user, boundary region 120 may be represented by a different representation than the representations of boundary region 116 and boundary region 118 (e.g., by a different color, a different line type, and the like). If the interpolation of the boundary regions is performed by an image processor, then the user can review the interpolated boundary region 120 of occluded segment 114 and adjust it, if necessary.

Since at least two images are acquired for each dye injection, from at least two different perspectives, at least two superimposed images are obtained. A three-dimensional (3D) model of occlusion area 102 is generated, using the at least two superimposed images, by methods known in the art. The 3D model includes a representation of both proximal segment 110 and distal segment 112. If the 3D model is generated using a larger number of images, acquired from different perspectives, then the 3D model can be more accurate and include more details of the blood vessels in the imaged body area (e.g., heart 100 of FIG. 1).

According to another embodiment of the disclosed technique, the 3D model of the occluded blood vessel can be generated by employing four fluoroscopic dye injections. With further reference to FIGS. 1 and 2, the first injection is administered to occluded artery 104, and is followed by acquiring a first image of proximal segment 110 of artery 104, from a first perspective. The second injection is administered to unblocked artery 106, and is followed by acquiring a first image of distal segment 112 of artery 104, from the first perspective. The third injection is administered to occluded artery 104, and is followed by acquiring a second image of proximal segment 110 of artery 104, from a second perspective (e.g., perpendicular to the first perspective). The fourth injection is administered to unblocked artery 106, and is followed by acquiring a second image of distal segment 112, from the second perspective. Two superimposed images are obtained by superimposing the 2D images acquired from each perspective. Each of the superimposed 2D images includes a representation of both proximal segment 110 and distal segment 112. Determining of the boundary regions of these segments and interpolating the boundary regions of occluded segment 114, can be performed, as described above. Subsequently, a 3D model of occlusion area 102 is determined, using the two superimposed images, by methods known in the art.

According to a further embodiment of the disclosed technique, the 3D model of the occluded blood vessel can be generated by superimposing two 3D models, one of the proximal segment and the other of the distal segment. This can be performed by employing four fluoroscopic dye injections and four acquired 2D images, each acquired from a different perspective. With further reference to FIGS. 1 and 2, a first injection is administered to occluded artery 104, and is followed by acquiring a first image of proximal segment 110 of artery 104, from a first perspective. A second injection is administered to unblocked artery 106, and is followed by acquiring a first image of distal segment 112 of artery 104, from a second perspective. A third injection is administered to occluded artery 104, and is followed by acquiring a second image of proximal segment 110 of artery 104, from a third perspective (e.g., perpendicular to the first perspective). A fourth injection is administered to unblocked artery 106, and is followed by acquiring a second image of distal segment 112, from the fourth perspective (e.g., perpendicular to the second perspective).

A first 3D model of proximal segment 110 is generated, using the 2D images including representations thereof (i.e., the 2D images acquired subsequent to the dye injections administered to occluded artery 104). A second 3D model of distal segment 112 is generated, using the 2D images including representations thereof (i.e., the 2D images acquired subsequent to the dye injections administered to unblocked artery 106). A complete 3D model of occlusion area 102 is generated, by combining the first 3D model of proximal segment 110 and the second 3D model of distal segment 112. Determining the boundary regions of proximal segment 110 and distal segment 112 and interpolating the boundary region of occluded segment 114, are performed on the complete 3D model, by image processing techniques known in the art. The boundary region of the occluded segment is determined while assuming that the occluded segment is substantially not tortuous.

Figure 8C:
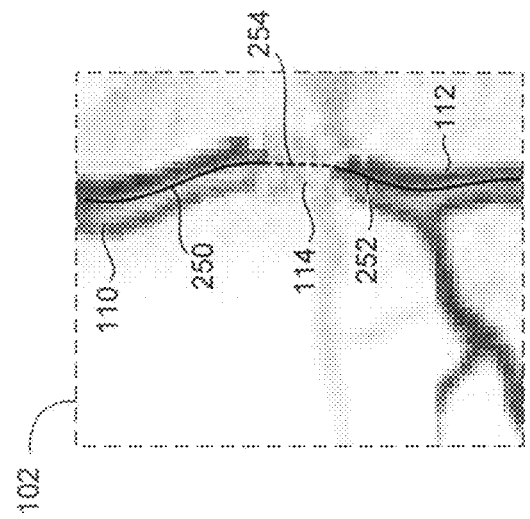
FIG. 8C is an enlarged view of the occlusion area of the heart of FIG. 1, including a proximal 3D safe trajectory, a distal 3D safe trajectory and an occlusion 3D safe trajectory.
Figure 8B:
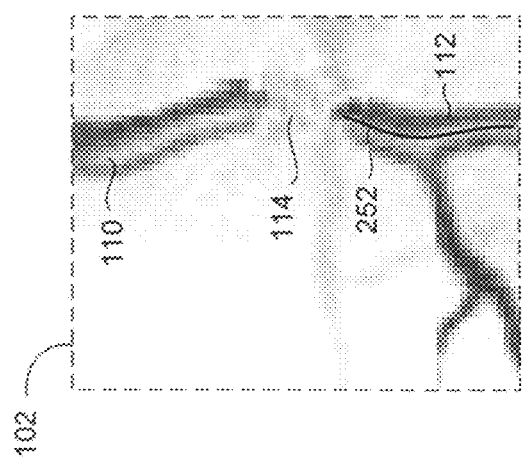
FIG. 8B is an enlarged view of the occlusion area of the heart of FIG. 1, including a distal 3D safe trajectory.
Figure 8A:
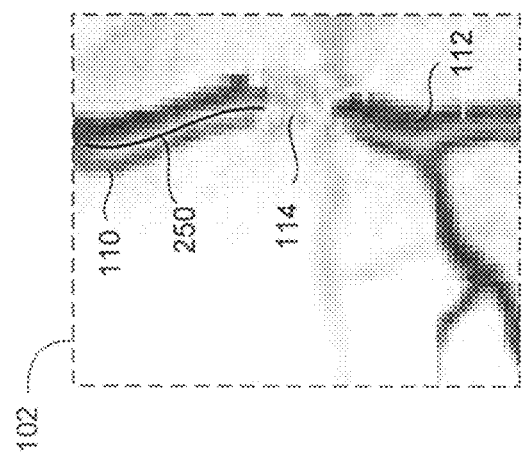
FIG. 8A is an enlarged view of the occlusion area of the heart of FIG. 1, including a proximal 3D safe trajectory, according to another embodiment of the disclosed technique.

Reference is now made to FIGS. 8A, 8B and 8C. FIG. 8A is an enlarged view of the occlusion area of the heart of FIG. 1, including a proximal 3D safe trajectory, according to another embodiment of the disclosed technique. FIG. 8B is an enlarged view of the occlusion area of the heart of FIG. 1, including a distal 3D safe trajectory. FIG. 8C is an enlarged view of the occlusion area of the heart of FIG. 1, including a proximal 3D safe trajectory, a distal 3D safe trajectory and an occlusion 3D safe trajectory. A first Guided Measurement Catheter (GMC, not shown) is inserted into occluded artery 104, approaching occluded segment 114 from proximal segment 110. As the first GMC tip is advanced within proximal segment 110, toward occluded segment 114, a respective GMC-related device (not shown) determines the 3D position and orientation of the first GMC tip, in a plurality of positions (not shown) along proximal segment 110. The GMC-related device thereby determines a continuous proximal 3D safe trajectory 250, through which the first GMC tip passed within proximal segment 110. The GMC-related device may be, for example, an MPS, wherein the first GMC is equipped with an MPS sensor on the tip thereof (i.e., similar to the MPS and MPS sensor of the system described herein below with reference to FIG. 5). Similarly, a second GMC (not shown) is inserted into occluded artery 104, approaching occluded segment 114 from distal segment 112. As the second GMC tip is advanced within distal segment 112 toward occluded segment 114, a respective GMC-related device determines the 3D position and orientation of the second GMC tip in a plurality of positions (not shown) along distal segment 112. The GMC-related device thus determines a continuous distal 3D safe trajectory 252, through which the second GMC tip passed within distal segment 112. Proximal 3D safe trajectory 250 and distal 3D safe trajectory 252 do not intersect, since neither one of the first GMC and the second GMC pass through occluded segment 114. An occlusion 3D safe trajectory 254 can then be determined, by interpolating between proximal 3D safe trajectory 250 and distal 3D safe trajectory 252. The proximal, distal and occluded 3D safe trajectories (250, 252 and 254, respectively) can be superimposed on the 3D model of occluded artery 104 (e.g., the 3D model as described with reference to FIGS. 4A, 4B and 4C). In this manner, the person performing the medical procedure described herein is provided with additional safe trajectory information within the occluded segment. The additional safe trajectory information may be considered as more reliable, since proximal 3D safe trajectory 250 and distal 3D safe trajectory 252 represent actual trajectories, along which the first and second GMCs were advanced. These actual trajectories are considered safe, since the GMCs have already passed there along, without causing arterial perforation or other arterial damage.

Figure 4B:
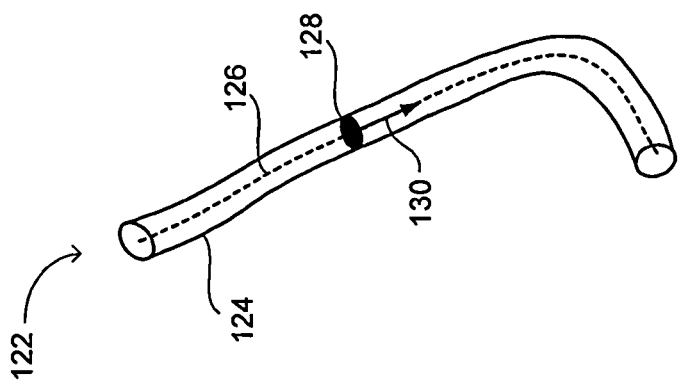
FIG. 4B is a schematic illustration of the 3D model of FIG. 4A, including a representation of an MPS sensor position and orientation, the orientation aligned with a 3D center line of the 3D model.
Figure 4A:
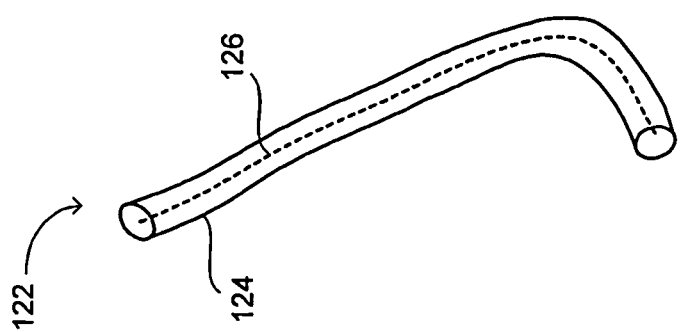
FIG. 4A is a schematic illustration of a 3D model of a blood vessel, generally referenced 122, similar to the occluded artery of FIG. 1, according to a further embodiment of the disclosed technique.

Reference is now made to FIGS. 4A, 4B and 4C. FIG. 4A is a schematic illustration of a 3D model of a blood vessel, generally referenced 122, similar to occluded artery 104 of FIG. 1, according to a further embodiment of the disclosed technique. FIG. 4B is a schematic illustration of the 3D model of FIG. 4A, including a representation of an MPS sensor position and orientation, the orientation aligned with a 3D center line of the 3D model. FIG. 4C is a schematic illustration of the 3D model of FIG. 4A, including a representation of an MPS sensor position and orientation, the orientation deviating from a 3D center line of the 3D model. 3D model 122 is generated (e.g., using acquired 2D images of the blood vessel from two different perspectives), subsequent to determining the boundary regions of the proximal segment, the occluded segment, and the distal segment of the occluded blood vessel. 3D model 122 includes a representation of vessel walls 124, and a reconstructed 3D center line 126. Reconstructed 3D center line 126 is an estimate of the actual center line of the blood vessel, generated according to the boundary regions of the occluded blood vessel. Reconstructed 3D center line 126 is determined for the overall blood vessel appearing in the acquired images, and passes through the proximal segment, the occluded segment, and the distal segment of the occluded blood vessel.

A medical procedure is performed on the occluded blood vessel, during which a guidewire is inserted into the blood vessel and passes through the occluded segment. In order to avoid the risk of localized arterial wall dissection or coronary perforation by the guidewire tip, the guidewire is to be advanced through the center of the occluded segment, along 3D center line 126. Thus, 3D center line 126 represents a 3D safe trajectory, through which the guidewire is to be advanced. With reference to FIG. 2A, the guidewire can approach occluded segment 114 from the proximal end thereof, passing first through proximal segment 110. Alternatively, the guidewire can approach occluded segment 114 from the distal end thereof, passing first through distal segment 112.

With reference to FIG. 4B, the guidewire is inserted into the blood vessel. The guidewire has an MPS sensor mounted on the distal tip thereof. The 3D position and 3D orientation of the MPS sensor are determined at a plurality of positions along the blood vessel, as the guidewire advances inside the blood vessel, by using an MPS, external to the body of the patient. 3D model 122 is registered with the 3D coordinate system of the MPS. The guidewire reaches an end of the occluded section (not shown) and is advanced through the occluded segment of the blood vessel (similar to occluded segment 114 of FIG. 2A). Representations of an MPS sensor position 128 and an MPS sensor orientation 130 are presented with respect to 3D model 122. MPS sensor position 128 indicates that the MPS sensor is located within the blood vessel, on 3D center line 126. MPS sensor orientation 130 indicates that the MPS sensor is advanced within the blood vessel, such that it is aligned with 3D center line 126.

3D model 122 is displayed to a user during the procedure of advancing the guidewire through the blood vessel. If MPS sensor orientation 130 is aligned with the safe trajectory, then MPS sensor orientation 130 or 3D center line 126 can be displayed in a positively related manner (e.g., using a green symbol or a green colored center line), indicating to the user that the guidewire is advanced along the safe trajectory, through the center of the occlusion, minimizing the risk of localized arterial wall dissection or coronary perforation.

With reference to FIG. 4C, the guidewire is advanced further into the occluded blood vessel. MPS sensor position 132 is located on the safe trajectory. MPS sensor orientation 134 deviates from the safe trajectory defined by 3D center line 126. In such a case, further advancing the guidewire tip may cause localized arterial wall dissection or perforation of the blood vessel. In order to avoid such cases, a notification is generated, indicating to the user that the guidewire deviates from the safe trajectory. For example, MPS sensor orientation 134 or 3D center line 126 can be displayed in a negatively related manner (e.g., using a red symbol or a red colored center line), an audio warning alarm can be sounded, and the like. Once the notification reaches the user, she can adjust the orientation of the guidewire, such that the guidewire is advanced along the safe trajectory.

According to another embodiment of the disclosed technique, a Computed Tomography (CT) 3D model of the occlusion area may be obtained by employing a preoperative CT scan. The CT 3D model can be registered with the 3D model generated subsequent to the fluoroscopic dye injections. The CT 3D model may include additional details of the occlusion area (relatively to the acquired 3D model), since it is generated from a relatively large number of 2D images (e.g., acquired from 64 perspectives). Such additional details may be, for example, the length of the occluded segment, the width of the occluded segment, the tortuosity of the occluded segment, and the like. These additional details may be superimposed on the acquired 3D model, after comparison with the CT 3D model, in order to enhance the acquired 3D model.

Figure 5:
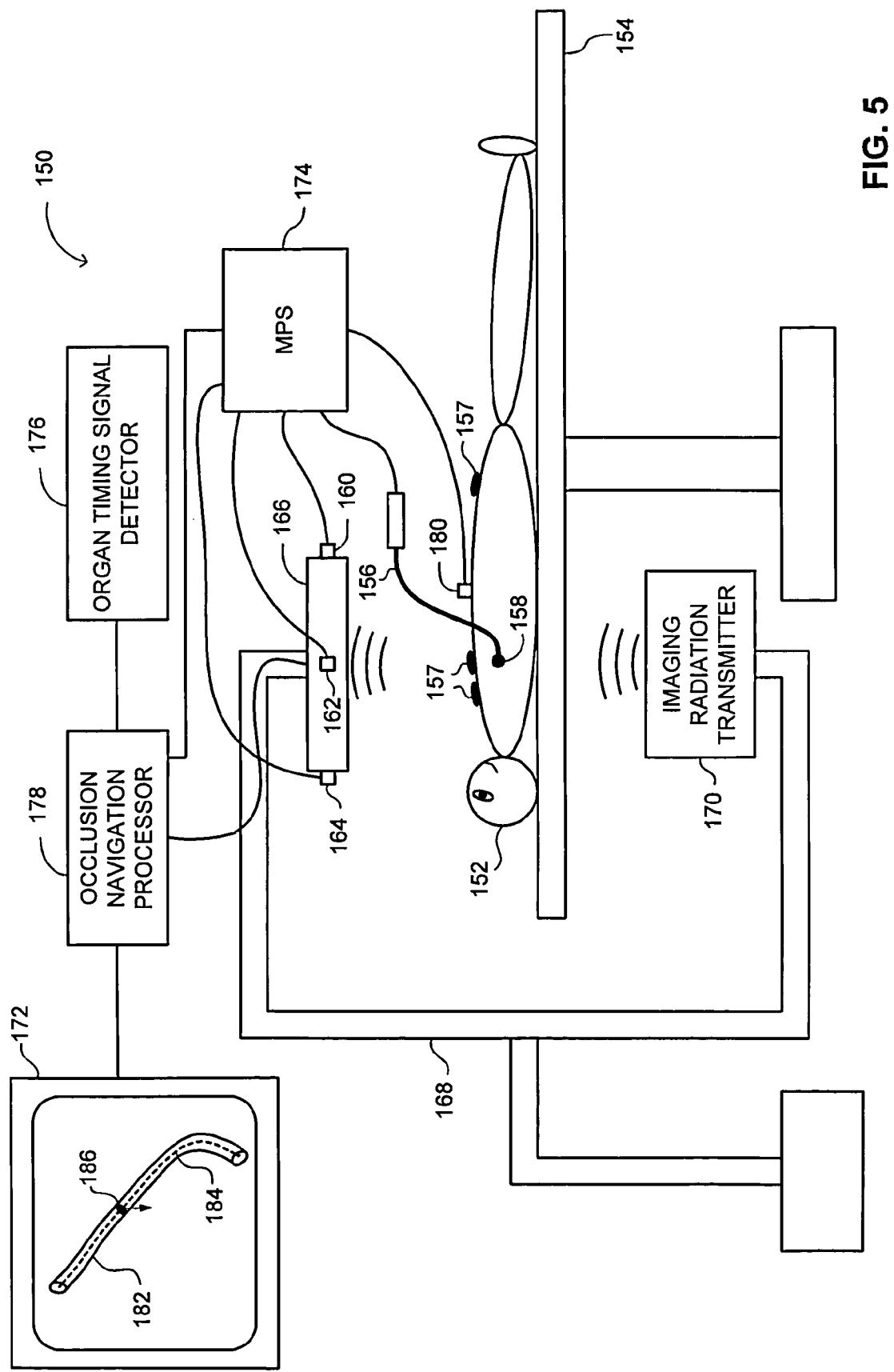
FIG. 5 is a schematic illustration of a system for generating a 3D model of an occluded tubular organ and navigating through the occlusion of the tubular organ, generally referenced 150, constructed and operative in accordance with a further embodiment of the disclosed technique.

Reference is now made to FIG. 5, which is a schematic illustration of a system for generating a 3D model of an occluded tubular organ and navigating through the occlusion of the tubular organ, generally referenced 150, constructed and operative in accordance with a further embodiment of the disclosed technique. System 150 includes a medical imaging system 168, a Medical Positioning System (MPS) 174, an organ timing signal detector 176, an occlusion navigation processor 178, a guidewire 156, a display 172 and a table 154. Medical imaging system 168 includes an imaging radiation transmitter 170 and an imaging radiation detector 166. Medical positioning system 174 includes MPS transmitters 160, 162 and 164, reference sensor 180 and an MPS sensor (not shown). Medical imaging system 168 may be an X-ray imaging system, in which imaging radiation transmitter 170 is an X-ray source and imaging radiation detector 166 is an X-ray detector (e.g., a film). Medical imaging system 168 may have the general shape of the letter "C" (i.e., a C-arm). A line (not shown) drawn between radiation transmitter 170 and radiation detector 166 defines an optical axis of medical imaging system 168. The term "perspective", as used herein, relates to the spatial orientation (i.e., vectorial direction) of the optical axis of medical imaging system 168 (i.e., the angle of the optical axis relative to patient 152).

Occlusion navigation processor 178 is coupled with organ timing signal detector 176, with imaging radiation detector 166, with MPS 174 and with display 172. MPS 174 is coupled with guidewire 156. The MPS sensor (not shown) is mounted on the distal end 158 of guidewire 156. MPS transmitters 160, 162 and 164 are coupled with imaging radiation detector 166. A patient 152 is placed on table 154. Patient 152 exhibits an occluded tubular organ (not shown), for example, an occluded coronary artery, similar to occluded artery 104 of FIG. 1. MPS 174 determines the position and orientation of the MPS sensor at a plurality of positions along the occluded tubular organ in a 3D coordinate system (hereinafter, the MPS coordinate system), relative to MPS transmitters 160, 162 and 164, and reference sensor 180.

A first fluoroscopic dye injection is administered to the occluded tubular organ, for example, by a physician. Medical imaging system 168 acquires a plurality of first-injection 2D images of the tubular organ from a plurality of different perspectives. The difference between the plurality of perspectives (i.e., the angular difference between the vectorial direction of the optical axis in each perspective) is at least 30°. Preferably, the difference between these perspectives is approximately 90°. Simultaneously to acquisition of the 2D images, organ timing signal detector 176 detects the activity state of the tubular organ. Thus, each acquired 2D image is associated with an organ timing signal reading. The organ timing signals can be detected by an Electrocardiogram (ECG) detector fitted with a plurality of body surface electrodes 157, placed on patient 152 (e.g., on the abdomen thereof). Since the occluded segment of the tubular organ does not allow blood to flow there through, the occluded segment and the distal segment do not appear in the first-injection 2D images. However, natural bypasses may allow blood flowing in the proximal segment to reach the distal segment. If such natural bypasses exist, then the distal segment shall appear in the first-injection 2D images (see FIG. 2B). If such natural bypasses do not exist, and the distal segment does not appear in the first-injection 2D images, then a second contra-lateral injection is administered (i.e., into another blood vessel). Blood flowing through the other blood vessel may flow through contra-lateral natural bypasses, and reach the distal segment. Subsequent to the second injection, medical imaging system 168 acquires a plurality of second-injection 2D images of the occlusion area from different perspectives, showing the presence of the fluoroscopic dye in the blood vessels in the heart of patient 152 (see FIG. 2C). In these images, the distal segment is visible, since blood containing the fluoroscopic dye flows there through. The proximal segment is not apparent in these images, since no fluoroscopic dye flows there through due to the second injection. It is noted, that the user of system 150 (e.g., a physician) may have prior knowledge regarding the degree of blockage in the occluded blood vessel (e.g., based on previous medical imaging, and the like). In this case, the physician may administer the second dye injection and use medical imaging system 168 to acquire the second-injection 2D images, without analyzing the first-injection 2D images (i.e., acquisition of the second-injection 2D images unconditionally of the results of the first-injection 2D images).

Since each pair of first-injection and second-injection 2D images is combined to form a single superimposed image, these first-injection and second-injection 2D images must be acquired at the same timing point of the organ timing cycle. In the case where video images are employed, the series of superimposed images are repeatedly displayed in continuum, to the user of system 150 (i.e., a recurring cyclic motion of the tubular organ). Thus, each displayed superimposed image appears in the respective timing point of the organ timing cycle, such that the video series of images accurately depicts the cyclic motion of the tubular organ.

Medical imaging system 168 provides the 2D images to occlusion navigation processor 178. When both the proximal segment and the distal segment appear in the acquired images, occlusion navigation processor 178 combines the images, generating a superimposed 2D image for each perspective. Each of the superimposed 2D images includes a representation of both ends of the occluded segment of the inspected tubular organ. For example, if two images were acquired for each dye injection, from two different perspectives, then occlusion navigation processor 178 can generate two superimposed 2D images.

Using image processing techniques, occlusion navigation processor 178 detects the boundary regions of the proximal segment and the distal segment of the tubular organ in each of the superimposed 2D images. Occlusion navigation processor 178 interpolates between the boundary regions of the distal and proximal segments, to provide an estimate of the boundary region of the occluded segment. A user of system 150 (e.g., a physician) observes the interpolated boundary region of the occluded segment and may manually reshape the interpolated boundary region (e.g., for necessary adjustments). For example, the user may alter the tortuosity of the interpolated boundary region, if she has prior knowledge of the actual tortuosity of the occluded segment. Alternatively, the user of system 150 can manually join between the boundary regions of the distal and proximal segments (i.e., manual interpolation). For example, the user can indicate the boundary region of the occluded segment by drawing connecting lines between the distal and proximal segments, as she sees fit, via an input module (not shown). Display 172 can display the boundary region of the occluded segment, with a different representation than the representations of the boundary regions of the proximal and distal segments (e.g., by a different color, a different line type, and the like).

Occlusion navigation processor 178 generates a 3D model 182 of the tubular organ, using the superimposed 2D images. Occlusion navigation processor 178 further determines an estimate for a 3D center line 184 of the tubular organ, according to 3D model 182. 3D center line 184 passes through the proximal segment, the occluded segment, and the distal segment of the occluded tubular organ. Display 172 provides a visual representation of 3D model 182 and a visual representation of 3D center line 184 of the tubular organ. Display 172 may further display 3D model 182 superimposed on a 2D image of the tubular organ, such as the superimposed image. Occlusion navigation processor 178 registers 3D model 182 with the MPS coordinate system of MPS 174. Display 172 provides a visual representation of the position and orientation 186 of the MPS sensor with respect to 3D model 182.

The user of system 150 inserts guidewire 156 into the tubular organ and advances it toward the occluded segment thereof. In order to avoid the risk of localized dissection or coronary perforation by guidewire distal tip 158, the user of system 150 should advance guidewire 156 without deviating from the centerline of the occluded segment (i.e., along 3D center line 184). Thus, 3D center line 184 represents a safe trajectory, through which guidewire distal tip 158 should be advanced.

The user of system 150 advances guidewire 156 further into the inspected tubular organ. When distal tip 158 progresses along 3D center line 184, display 172 provides a visual representation of MPS sensor position and orientation 186 with a positively related manner (e.g., using a green arrow or a first predetermined audible sound). In this manner, the user is assured that it is safe to advance the guidewire through the center of the occlusion, minimizing the risk of localized dissection or coronary perforation.

If guidewire 156 deviates from the safe trajectory and the user further advances guidwire distal tip 158, then guidewire distal tip 158 may cause localized dissection or perforation of the tubular organ. In order to avoid such cases, occlusion navigation processor 178 generates a indication, indicating to the user that guidewire distal tip 158 deviates from the safe trajectory. For example, display 172 can provide a visual representation of MPS sensor position and orientation 186 with a negatively related notification (e.g., using a red arrow), occlusion navigation processor 178 can produce an audio notification warning sound, and the like. Once the indication reaches the user, she can adjust the orientation of guidewire distal tip 158, such that the orientation of guidewire distal tip 158 is aligned with the safe trajectory, or refrain from advancing the guidewire.

According to a further embodiment of the disclosed technique, the user of system 150 advances the guidewire, while observing the guidewire distal tip using the medical imaging system (without using the MPS). The medical imaging system produces images, in which the distal tip of the guidewire is visible, in addition to the occluded tubular organ. The user advances the distal tip of the guidewire along the 3D center line (i.e., the safe trajectory), as reconstructed by the occlusion navigation processor. Since the images generated by the medical imaging system are 2D images, occlusion navigation processor employs image processing techniques to project the 2D images on the 3D model of the tubular organ. According to the present embodiment, the distal tip of the guidewire is not equipped with an MPS sensor, and the user navigates the distal tip through the tubular organ, according to the distal tip location as it appears in the images of the medical imaging system.

When guidewire distal tip 158 reaches the distal segment of the occluded tubular organ, the user can then pass a catheter over the guidewire, for treating the occluded blood vessel. Such a catheter may be a Guided Measurement Catheter (GMC), a diagnostic catheter (e.g., Ultra Sound imaging catheter), or an ablation catheter. For example, the user can perform angioplasty, by inserting a balloon catheter into the blood vessel, and inflating the balloon within the occluded segment, in order to dilate the occluded blood vessel.

According to another embodiment of the disclosed technique, the parallel-wire technique may be applied to the occluded tubular organ. When the user advances the guidewire into the tubular organ, the guidewire may create a false lumen, usually in the subintimal space of the occluded segment. According to the parallel-wire technique, the guidewire is then left within the false lumen, and a second guidewire (not shown) is inserted into the tubular organ, along the first guidewire. The second guidewire usually has a different shape than the first guidewire. The second guidewire will not enter the false lumen created by the first guidewire, and will attempt to find the true lumen in the occluded tubular organ (i.e., the lumen which will eventually lead to the distal end of the occluded segment). Thus, the first guidewire acts as a landmark designating the false lumen. Both guidewires have an MPS sensor mounted on the distal tip thereof. Thus, the trace of advancement of the first wire is known (i.e., according to the MPS reading of the respective MPS sensor) and may be displayed to the user. When inserting the second guidewire, the user can then clearly observe the course of the false lumen, and advance the second guidewire along a different course, attempting to find the true lumen.

Figure 6:
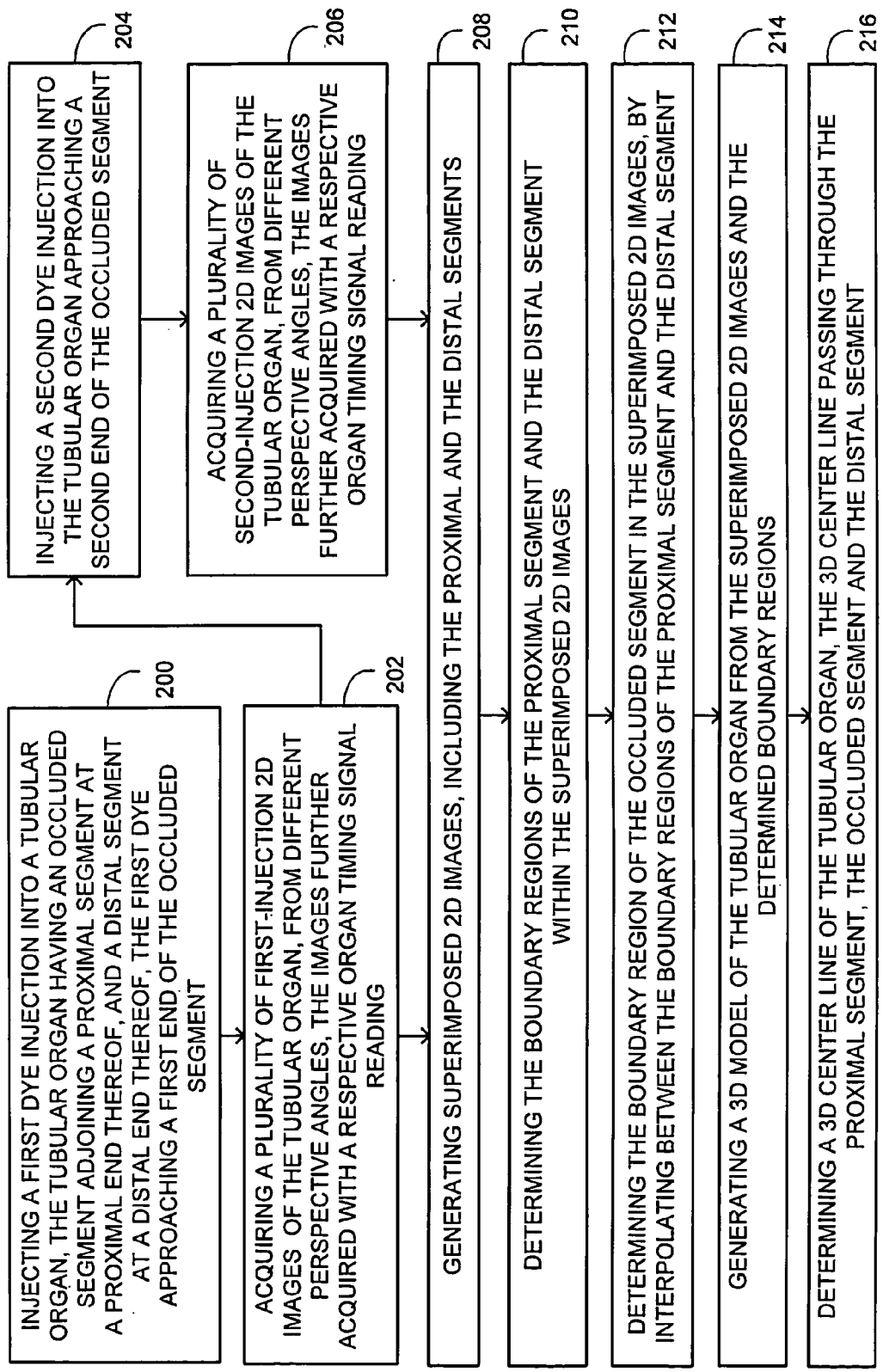
FIG. 6 is a schematic illustration of a method for generating a three dimensional (3D) model of an occluded tubular organ, according to another embodiment of the disclosed technique.

Reference is now made to FIG. 6, which is a schematic illustration of a method for generating a three dimensional (3D) model of an occluded tubular organ, according to another embodiment of the disclosed technique. The tubular organ has an occluded segment adjoining a proximal segment at a proximal end thereof, and a distal segment at a distal end thereof. In procedure 200, a first dye injection is administered into the tubular organ, the first dye approaching a first end of the occluded segment. With reference to FIGS. 2A and 5, a physician administers a first fluoroscopic dye injection into the tubular organ of patient 152 (such as occluded artery 104). The fluoroscopic dye approaches occluded segment 114 through proximal segment 110.

In procedure 202, a plurality of first-injection 2D images of the tubular organ is acquired, from different perspectives. The images are further acquired with a respective organ timing signal reading. With reference to FIGS. 2B and 5, medical imaging system 168 acquires a plurality of first-injection 2D images of the tubular organ from different of perspective angles, subsequent to the first dye injection. First-injection 2D image 103 exhibits the presence of the fluoroscopic dye in the blood vessels in heart 100 subsequent to the first dye injection. Simultaneously to acquisition of the first-injection 2D images, organ timing signal detector 176 detects the activity state of the tubular organ. Thus, each acquired 2D image is associated with an organ timing signal reading. The organ timing signals can be detected by an Electrocardiogram (ECG) detector fitted with body surface electrodes placed on patient 152.

If the distal segment is not apparent in the first-injection 2D images, then the method depicted in FIG. 6 continues from procedure 202 to procedure 204. In procedure 204, a second dye injection is administered into the tubular organ, the second dye approaching the other end of the occluded segment. With reference to FIGS. 2A, 2C and 5, if distal segment 112 is not apparent in the first-injection 2D images, then the physician administers a second contra-lateral fluoroscopic dye injection into unblocked artery 106. Blood flowing through unblocked artery 106 may flow through natural bypass 108, and reach distal segment 112.

In procedure 206, a plurality of second-injection 2D images of the tubular organ is acquired, from different perspectives. The images are further acquired with a respective organ timing signal reading. With reference to FIG. 5, medical imaging system 168 acquires a plurality of second-injection 2D images of the tubular organ from different of perspectives, subsequent to the second dye injection. With reference to FIG. 2C, second-injection 2D image 105 exhibits the presence of the fluoroscopic dye in the blood vessels in heart 100 subsequent to the second dye injection. In 2D image 105, distal segment 112 is visible, while proximal segment 110 is not visible. Simultaneously to acquisition of the second-injection 2D images, organ timing signal detector 176 detects the activity state of the tubular organ. Thus, each acquired 2D image is associated with an organ timing signal reading.

If the distal segment is apparent in the first-injection 2D images, then the method depicted in FIG. 6 continues from procedure 202 to procedure 208. In procedure 208, a plurality of superimposed 2D images is generated from the plurality of acquired 2D images subsequent to each dye injection. The superimposed 2D images include a representation of the proximal segment and the distal segment. With reference to FIGS. 5, 2B and 2C, medical imaging system 168 provides the first-injection and second-injection 2D images (such as first-injection 2D image 103 and second-injection 2D image 105) to occlusion navigation processor 178. When both the proximal segment and the distal segment appear in the acquired images, occlusion navigation processor 178 combines the images, generating a superimposed 2D image (such as the 2D image of FIG. 2A) for each perspective. Each of the superimposed 2D images includes a representation of both ends of the occluded segment of the inspected tubular organ.

In procedure 210, the boundary regions of the proximal segment and the distal segment are determined within the superimposed 2D images. With reference to FIGS. 3A and 5, occlusion navigation processor 178 detects the boundary regions of the proximal segment (such as boundary region 116 of proximal segment 110) and the distal segment (such as boundary region 118 of distal segment 112) of the tubular organ in each of the superimposed 2D images, using image processing techniques.

In procedure 212, the boundary regions of the occluded segment are determined in the superimposed 2D images, by interpolating between the boundary regions of the proximal segment and the distal segment. With reference to FIGS. 3B and 5, occlusion navigation processor 178 interpolates between the boundary regions of the distal and proximal segments, to provide an estimate of the boundary region of the occluded segment (such as boundary region 120 of occluded segment 114). Alternatively, the user of system 150 can manually join between the boundary regions of the distal and proximal segments (i.e., manual interpolation). For example, the user can indicate the boundary region of the occluded segment by drawing connecting lines between the distal and proximal segments, as she sees fit, via an input module (not shown).

In procedure 214, a 3D model of the tubular organ is generated from the superimposed 2D images and the determined boundary regions. With reference to FIG. 5, occlusion navigation processor 178 generates a 3D model 182 of the tubular organ, using the superimposed 2D images.

In procedure 216, a 3D center line of the tubular organ is determined, the 3D center line passing through the proximal segment, the occluded segment and the distal segment. With reference to FIG. 5, occlusion navigation processor 178 further determines an estimate for a 3D center line 184 of the tubular organ, according to 3D model 182. 3D center line 184 passes through the proximal segment, the occluded segment, and the distal segment of the occluded tubular organ.

Figure 7:
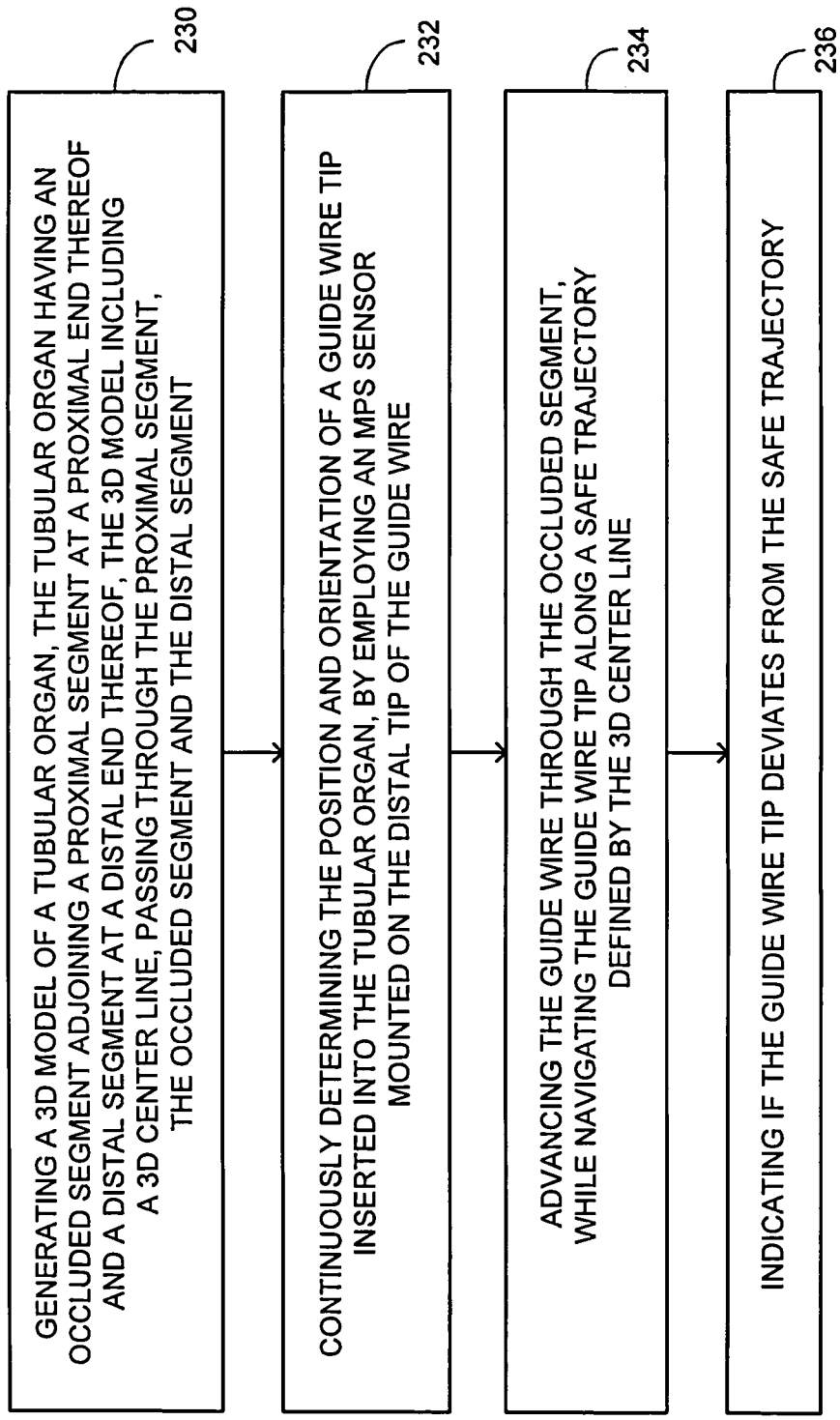
FIG. 7 is a schematic illustration of a method for navigating through a tubular organ, according to a further embodiment of the disclosed technique.

Reference is now made to FIG. 7, which is a schematic illustration of a method for navigating through a tubular organ, according to a further embodiment of the disclosed technique. The tubular organ exhibits an occluded segment adjoining a proximal segment at a proximal end thereof, and a distal segment at a distal end thereof. In procedure 230, a 3D model of the tubular organ is generated. The 3D model includes a 3D center line, passing through the proximal segment, the occluded segment and the distal segment. With reference to FIG. 5, occlusion navigation processor 178 generates a 3D model 182 of the tubular organ. Occlusion navigation processor 178 further determines an estimate for a 3D center line 184 of the tubular organ, according to 3D model 182. 3D center line 184 passes through the proximal segment, the occluded segment, and the distal segment of the occluded tubular organ.

In procedure 232, the position and orientation of a guidewire tip, inserted into the tubular organ are determined at a plurality of positions along the tubular organ, by employing an MPS sensor mounted on the distal tip of the guidewire. With reference to FIG. 5, guidewire 156 is inserted into the tubular organ and approaches the occluded segment thereof. MPS 174 determines the position and orientation of the MPS sensor mounted on distal tip 158 with respect to the inspected tubular organ, with respect to the MPS coordinate system, defined by MPS transmitters 160, 162 and 164, and reference sensor 180.

According to a further embodiment of the disclosed technique, the user of system 150 advances the guidewire, while observing the guidewire distal tip using the medical imaging system (without using the MPS). The medical imaging system produces images, in which the distal tip of the guidewire is visible, in addition to the occluded tubular organ. The user advances the distal tip of the guidewire along the 3D center line (i.e., the safe trajectory), as reconstructed by the occlusion navigation processor. Since the images generated by the medical imaging system are 2D images, occlusion navigation processor employs image processing techniques to project the 2D images on the 3D model of the tubular organ. According to the present embodiment, the distal tip of the guidewire is not equipped with an MPS sensor, and the user navigates the distal tip through the tubular organ, according to the distal tip location as it appears in the images of the medical imaging system.

In procedure 234, the guidewire is advanced through the occluded segment, while the guidewire tip is navigated along a safe trajectory defined by the 3D center line. With reference to FIG. 5, the user (e.g., a physician, a robotic arm, and the like) of system 150 advances guidewire 156 further into the inspected tubular organ, along the safe trajectory defined by 3D center line 184. Alternatively, the guidewire is not equipped with an MPS sensor, and the user of system 150 navigates the distal tip of the guidewire according to the appearance thereof in images produced by the medical imaging system.

In procedure 236, an indication is produced if the guidewire tip deviates from the safe trajectory. With reference to FIG. 5, if guidewire 156 deviates from the safe trajectory and the user further advances guidwire distal tip 158, then guidwire distal tip 158 may cause localized dissection or perforation of the tubular organ wall. In order to avoid such dissection or perforation, occlusion navigation processor produces an indication, indicating to the user that guidewire distal tip 158 deviates from the safe trajectory. For example, display 172 can provide a visual representation of MPS sensor position and orientation 186 with a negatively related notification (e.g., using a red arrow), occlusion navigation processor 178 can produce an audio notification warning sound, and the like.

It will be appreciated by persons skilled in the art that the disclosed technique is not limited to what has been particularly shown and described hereinabove. Rather the scope of the disclosed technique is defined only by the claims, which follow.

The invention claimed is:

1. A system for generating a 3D model of an occluded tubular organ of a patient and navigating through the tubular organ, the tubular organ having an occluded segment adjoining a proximal segment at a proximal end thereof, and a distal segment at a distal end thereof, the system comprising:
   a medical imaging system including an imaging radiation transmitter and an imaging radiation detector, said medical imaging system being configured to acquire first and second first-injection two-dimensional (2D) images of said tubular organ respectively from first and second perspectives and first and second second-injection two-dimensional (2D) images of said tubular organ respectively from said first and second perspectives;
   an organ timing signal detector, for detecting the activity state of said tubular organ, simultaneously with the acquisition of said 2D images;
   a Medical Positioning System (MPS) configured to determine the position and orientation of a guidewire tip inserted into said tubular organ, at a plurality of positions along said tubular organ, said MPS including a plurality of MPS transmitters, coupled with said medical imaging system, a reference sensor, coupled with the body of said patient, and an MPS sensor, coupled with the tip of said guidewire;
   an occlusion navigation processor, coupled with said medical imaging system, said organ timing signal detector, and said MPS, said occlusion navigation processor being configured to generate a first superimposed 2D image associated with said first perspective by combining said first first-injection image and said first second-injection image, and a second superimposed 2D image associated with said second perspective by combining said second first-injection image and said second second-injection image, each of said first and second superimposed 2D images including a respective representation of said proximal segment and said distal segment, said occlusion navigation processor being configured to determine respective boundary regions of said proximal segment and said distal segment in said first and second superimposed 2D images, said occlusion navigation processor being configured to determine, for each of said first and second superimposed 2D images, a respective boundary region of said occluded segment by interpolating between said boundary regions of said proximal segment and said distal segment in each of said first and second superimposed 2D images, said occlusion navigation processor being configured to generate a 3D model of said tubular organ from said first and second superimposed 2D images and said determined boundary regions, said occlusion navigation processor being configured to determine a 3D center line of said tubular organ according to the boundary region of said occluded segment, said 3D center line passing through said proximal segment, said occluded segment and said distal segment, said 3D center line defining a safe trajectory at least within said occluded segment of said tubular organ.

2. A system according to claim 1, wherein said occlusion navigation processor produces an indication when said guidewire tip deviates from said safe trajectory.

3. A system according to claim 1, further comprising a display, coupled with said occlusion navigation processor, configured to provide a visual representation of said 3D center line and of the position and orientation of said MPS sensor.

4. A system according to claim 3, wherein said display further provides a visual representation of an indication when said guidewire tip deviates from said safe trajectory, said indication produced by said occlusion navigation processor.

5. The system according to claim 1 wherein each of said superimposed 2D images are based on respective 2D images of said tubular organ acquired at the same timing point of the organ timing signal.

6. The system according to claim 1 wherein said determined boundary region of said occluded segment in said superimposed 2D images is an interpolated estimate and wherein said system is further configured to allow a user to manually reshape the interpolated boundary region.

7. The system according to claim 3 wherein said display is configured to display the boundary region of said occluded segment with a representation that is different from that of the boundary regions of said proximal and distal segments.

8. The system according to claim 7 wherein said occluded segment representation is one selected from the group comprising a color different from that used for the boundary regions of said proximal and distal segments and a line type different from that used for the boundary regions of said proximal and distal segments.

9. The system according to claim 1 wherein said organ timing signal is indicative of cyclic motion of said tubular organ according to the cardiac cycle and respiration.

10. A system for generating a 3D model of an occluded tubular organ of a patient and navigating through the tubular organ, the tubular organ having an occluded segment adjoining a proximal segment at a proximal end thereof, and a distal segment at a distal end thereof, the system comprising:
   a medical imaging system configured to acquire, from a first perspective and a second, different perspective, a respective plurality of 2D images of said tubular organ, wherein each plurality collectively includes said proximal and distal segments;
   an organ timing signal detector configured to detect the activity state of said tubular organ simultaneously with the acquisition of said 2D images;
   Medical Positioning System (MPS) configured to determine the position and orientation of a guidewire tip in said tubular organ at a plurality of positions along said tubular organ, said MPS including an MPS sensor coupled with the tip of said guidewire;
   an occlusion navigation processor, coupled with said medical imaging system, said organ timing signal detector and said MPS, configured (i) to generate, for each of said first and second perspectives, a respective superimposed 2D image from said plurality of acquired 2D images associated with each of said first and second perspective, wherein each superimposed 2D image includes a representation of said proximal segment and said distal segment; (ii) to determine respective boundary regions of said proximal segment and said distal segment in each of said generated superimposed 2D images; (iii) to determine a respective boundary region of said occluded segment in each of said superimposed 2D images by interpolating, in each individual superimposed 2D image, between respective boundary regions of said proximal segment and said distal segment; (iv) to generate a 3D model of said tubular organ from said superimposed 2D images and said determined boundary regions; (v) to determine a 3D center line of said tubular organ according to the boundary region of said occluded segment in said 3D model, said 3D center line passing through said proximal segment, said occluded segment and said distal segment, said 3D center line defining a safe trajectory at least within said occluded segment of said tubular organ.

11. A system of claim 10, further comprising a display, coupled with said occlusion navigation processor, configured to provide a visual representation of said 3D center line and of the position and orientation of said MPS sensor.

12. The system of claim 10 wherein each of said superimposed 2D images are based on respective 2D images of said tubular organ acquired at the same timing point of the organ timing signal.

13. The system of claim 10 wherein said determined boundary regions of said occluded segment in said superimposed 2D images is an interpolated estimate and wherein said system is further configured to allow a user to manually reshape the interpolated boundary regions.

14. The system of claim 11 wherein said display is configured to display the boundary region of said occluded segment with a representation that is different from that of the boundary regions of said proximal and distal segments.

15. The system of claim 14 wherein said occluded segment representation is one selected from the group comprising a color different from that used for the boundary regions of said proximal and distal segments and a line type different from that used for the boundary regions of said proximal and distal segments.

16. The system of claim 10 wherein said organ timing signal is indicative of cyclic motion of said tubular organ according to the cardiac cycle and respiration.

17. The system of claim 1 wherein said first and second perspectives of said first and second superimposed 2D images, relates to the vectorial direction of the optical axis of an imaging device acquiring said first-injection 2D images and second-injection 2D images, and wherein the difference between said first and second perspectives is at least 30°.

18. The system of claim 17 wherein the difference between said first and second perspectives is approximately 90°.

19. The system of claim 1, wherein said first-injection 2D images are acquired when a first dye is injected so as to approach a first end of said occluded segment, and said second-injection 2D images are acquired when a second dye is injected so as to approach a second end of said occluded segment, said second-injection 2D images being acquired when said second end of said occluded segment is not visible in said first-injection 2D images.

* * * * *